US009539202B2

(12) United States Patent
Herrero Vanrell et al.

(10) Patent No.: US 9,539,202 B2
(45) Date of Patent: Jan. 10, 2017

(54) FORMULATION OF LIPOSOMAL VESICLES IN AQUEOUS SOLUTIONS WITH LACHRYMAL FILM CHARACTERISTICS

(75) Inventors: Rocio Herrero Vanrell, Madrid (ES); Jose Benitez Del Castillo, Madrid (ES); Eva Vico Ruiz, Madrid (ES); Marta Vicario De La Torre, Madrid (ES); Irene Teresa Molina Martinez, Madrid (ES)

(73) Assignee: UNIVERSIDAD COMPLUTENSE DE MADRID, Madrid (ES)

( * ) Notice: Subject to any disclaimer, the term of this patent is extended or adjusted under 35 U.S.C. 154(b) by 0 days.

(21) Appl. No.: 11/796,747

(22) Filed: Apr. 27, 2007

(65) Prior Publication Data
US 2007/0292496 A1    Dec. 20, 2007

Related U.S. Application Data

(60) Provisional application No. 60/796,118, filed on Apr. 28, 2006.

(51) Int. Cl.
| | |
|---|---|
| *A61K 9/127* | (2006.01) |
| *A61K 31/00* | (2006.01) |
| *A61K 31/70* | (2006.01) |
| *A61K 31/728* | (2006.01) |
| *A61K 38/00* | (2006.01) |
| *A61K 9/00* | (2006.01) |
| *A61K 31/07* | (2006.01) |
| *A61K 31/20* | (2006.01) |
| *A61K 31/375* | (2006.01) |
| *A61K 31/56* | (2006.01) |
| *A61K 33/00* | (2006.01) |
| *A61K 38/17* | (2006.01) |
| *A61K 38/18* | (2006.01) |
| *A61K 38/30* | (2006.01) |
| *A61K 38/38* | (2006.01) |
| *A61K 38/40* | (2006.01) |
| *A61K 38/47* | (2006.01) |
| *A61K 38/57* | (2006.01) |

(52) U.S. Cl.
CPC ............ *A61K 9/0048* (2013.01); *A61K 9/127* (2013.01); *A61K 31/07* (2013.01); *A61K 31/20* (2013.01); *A61K 31/375* (2013.01); *A61K 31/56* (2013.01); *A61K 33/00* (2013.01); *A61K 38/1709* (2013.01); *A61K 38/1808* (2013.01); *A61K 38/1825* (2013.01); *A61K 38/1841* (2013.01); *A61K 38/30* (2013.01); *A61K 38/38* (2013.01); *A61K 38/40* (2013.01); *A61K 38/47* (2013.01); *A61K 38/57* (2013.01)

(58) Field of Classification Search
CPC ...... A61K 9/0048; A61K 9/127; A61K 31/00; A61K 31/70; A61K 31/728; A61K 38/00; A61K 38/1709

USPC ..................... 424/78.04, 427, 450
See application file for complete search history.

(56) References Cited

U.S. PATENT DOCUMENTS

| | | | |
|---|---|---|---|
| 4,421,748 A | 12/1983 | Trager et al. | |
| 4,804,539 A * | 2/1989 | Guo et al. | 424/450 |
| 4,818,537 A | 4/1989 | Guo | |
| 4,973,580 A | 11/1990 | Mascellani et al. | |
| 5,637,315 A * | 6/1997 | Zern et al. | 424/450 |
| 5,897,879 A * | 4/1999 | Friedman et al. | 424/486 |
| 6,162,801 A * | 12/2000 | Kita | 514/167 |
| 6,455,511 B1 | 9/2002 | Kampinga et al. | |
| 6,555,526 B2 * | 4/2003 | Matsuo | A61K 9/0048 514/53 |
| 6,656,460 B2 | 12/2003 | Benita et al. | |
| 7,514,099 B2 * | 4/2009 | Chen et al. | 424/450 |
| 2001/0005501 A1 * | 6/2001 | Marriott | A61K 9/0014 424/1.21 |
| 2003/0105055 A1 * | 6/2003 | Demers | 514/44 |
| 2004/0077603 A1 * | 4/2004 | Stoffel | 514/78 |

OTHER PUBLICATIONS

Brown et al, J. Eur. Acad. Dermatol. Venereol. 19(3):308-318, 2004; available online Nov. 19, 2004.*
Mculley, J.P., et al "A compositional based Model for the Tear Film Lipid Layer" (1997) vol. XC, pp. 79-93.
Stern, M. E. "The Diagnosis and Management of Dry Eye" *Cornea* (2000) vol. 19 pp. 644-649.
Ibrahim, H., et al "Composition, structure et parametres physiologiques du systeme lacrymal impliques dans la conception des formes ophtalmiques" *Pharm Acta Hel* (1988) vol. 63 pp. 146-154.
Brignole, F., P.-J. Pisella, et al. (2005). "Efficacy and safety of 0.18% sodium hyaluronate in patients with moderate dry eye syndrome and superficial keratitis." *Graefe's Archive for Clinical and Experimental Ophthalmology* 243(6): 531-538.
Debbasch C, B. F., Pisella PJ, Warnet JM, Rat P, Baudouin C (2001). "Quaternary ammoniums and other preservatives' contribution in oxidative stress and apoptosis on Chang conjunctival cells." *Investigative Ophthalmology and Visual Science* 42(3): 642-52.
Gipson, I. K., Y. Hori, et al. (2004). "Character of Ocular Surface Mucins and their Alteration in Dry Eye Disease." *The Ocular Surface* 2(2): 131-148.
Gomes, J. A. P., R. Amankwah, et al. (2004). "Sodium hyaluronate (hyaluronic acid) promotes migration of human corneal epithelial cells in vitro." *British Journal of Ophthalmology* 88(6): 821-825.

(Continued)

*Primary Examiner* — Kevin Hill
(74) *Attorney, Agent, or Firm* — Ladas & Parry LLP

(57) ABSTRACT

The present invention involves the preparation of a pharmaceutical liposomal system in an aqueous solution which contains a substance or polymer with mucomimetic and/or mucoadhesive properties. Due to the components and characteristics of the formulation described in this present patent it can be used as a precorneal tear film substitute. This invention is included in the pharmacy and medicine areas.

19 Claims, 4 Drawing Sheets

(56) References Cited

OTHER PUBLICATIONS

Krause, W. E., E. G. Bellomo, et al. (2001). "Rheology of Sodium Hyaluronate under Physiological Conditions." *Biomacromolecules* 2(1): 65-69.

Lim, S. T., G. P. Martin, et al. (2000). "Preparation and evaluation of the in vitro drug release properties and mucoadhesion of novel microspheres of hyaluronic acid and chitosan." *Journal of Controlled Release* 66(2-3): 281-292.

Mochizuki, H., M. Yamada, et al. (2008). "Fluorophotometric measurement of the precorneal residence time of topically applied hyaluronic acid." *British Journal of Ophthalmology* 92(1): 108-111.

Pandit, J. C., B. Nagyová, et al. (1999)."Physical Properties of Stimulated and Unstimulated Tears." *Experimental Eye Research* 68(2): 247-253.

Pirnazar, P., L. Wolinsky, et al. (1999). "Bacteriostatic Effects of Hyaluronic Acid." *Journal of Periodontology* 70(4): 370-374.

Pritchard, K., A. B. Lansley, et al. (1996). "Evaluation of the bioadhesive properties of hyaluronan derivatives: Detachment weight and mucociliary transport rate studies." *International Journal of Pharmaceutics* 129(1-2):137-145.

Sellers, L. A., A. Allen, et al. (1991). "The rheology of pig small intestinal and colonic mucus: weakening of gel structure by non-mucin components." *Biochimica et Biophysica Acta (BBA)—General Subjects* 1115(2):174-179.

Van Santvlict, L. and A. Ludwig (1999). "Influence of the physico-chemical properties of ophthalmic viscolysers on the weight of drops dispensed from a flexible dropper bottle." *European Journal of Pharmaceutical Sciences* 7(4): 339-345.

Kogan, G., L. Soltés, et al. (2007). "Hyaluronic acid: a natural biopolymer with a broad range of biomedical and industrial applications." *Biotechnology Letters* 29(1): 17-25.

Yong-Hong, L., S. Jones, et al. (2005). "Hyaluronan: Pharmaceutical Characterization and Drug Delivery." *Drug Delivery* 12(6): 327-342.

McDonald C.C., Kaye S.B., Figueiredo F.C., Macintosh G., Lockett C. (2002) "A randomised, crossover, multicentre study to compare the performance of 0.1% (w/v) sodium hyaluronate with 1.4% (w/v) polyvinyl alcohol in the alleviation of symptoms associated with dry eye syndrome" *Eye* 16: 601-607.

Vicario-de-la-Torre, et a., Design and characterization of an ocular topical liposomal preparation to replenish the lipids of the tear film. *Invest Ophthalmol Vis Sci* 2014:55:7839-7847.

* cited by examiner

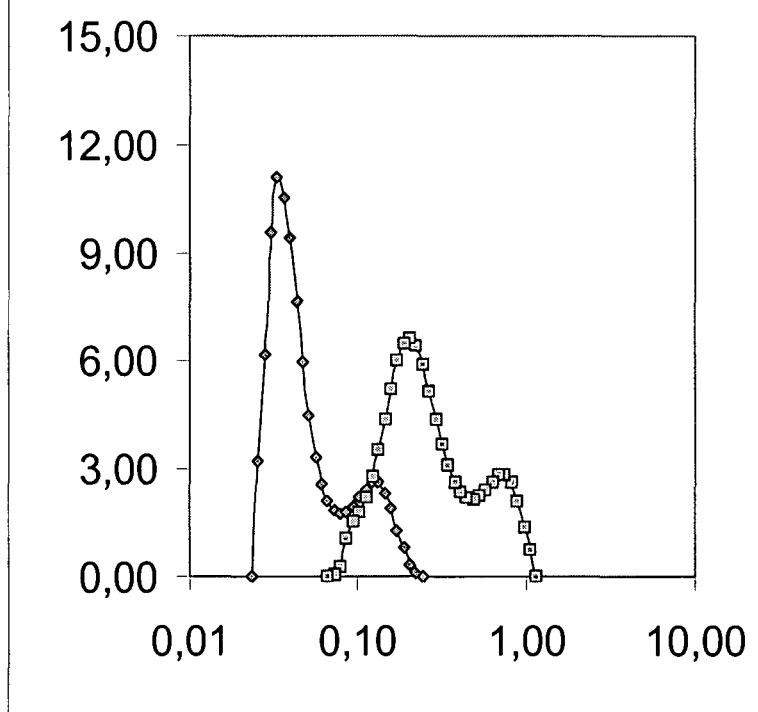

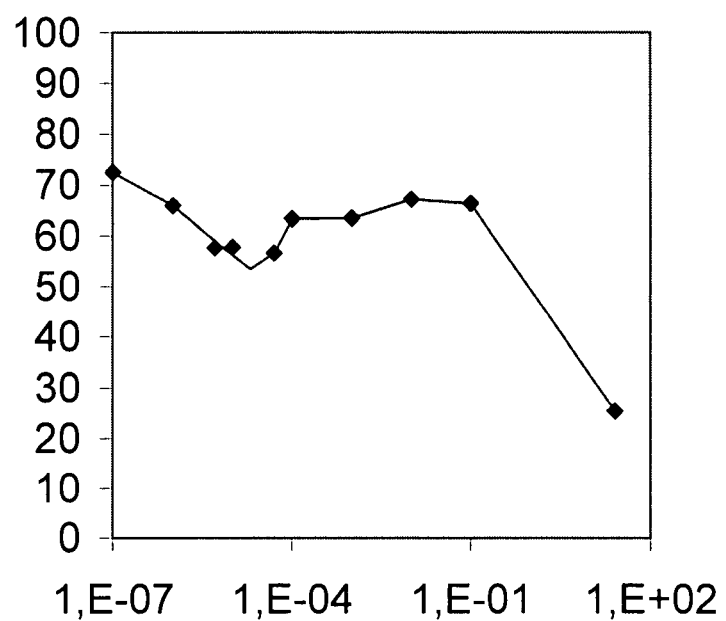

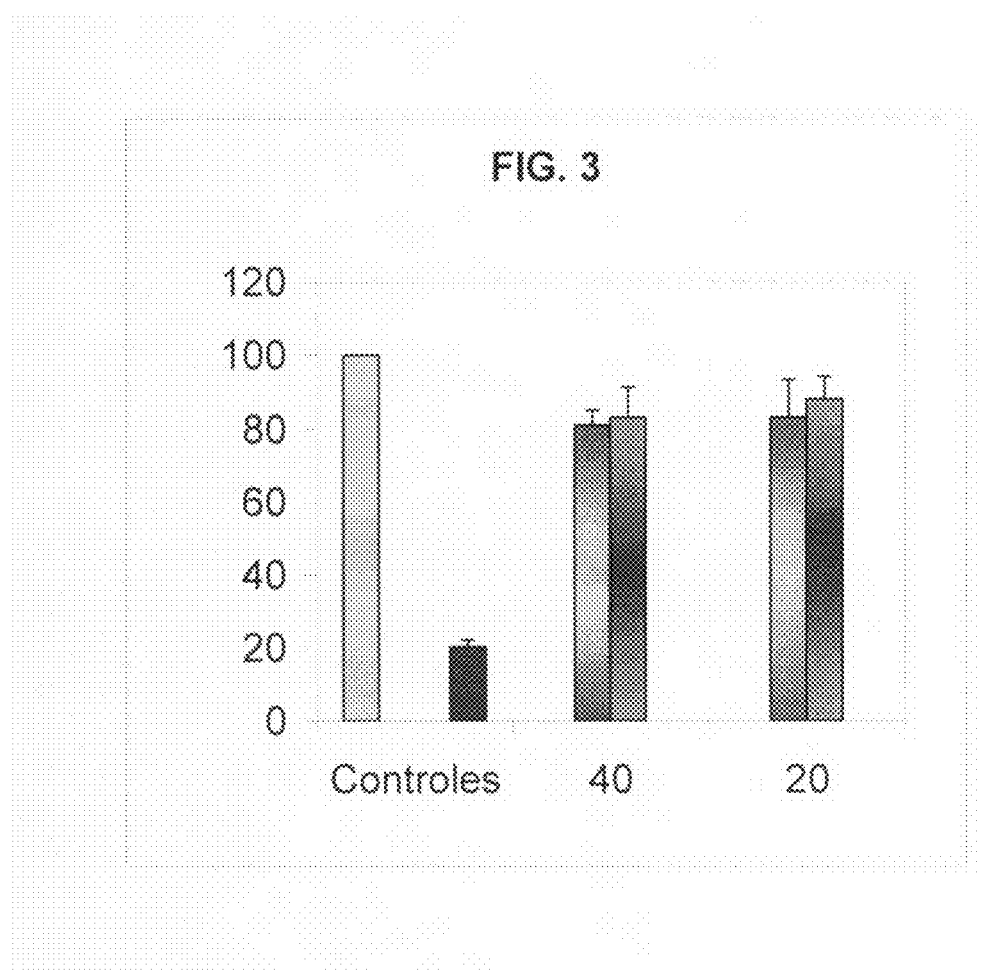

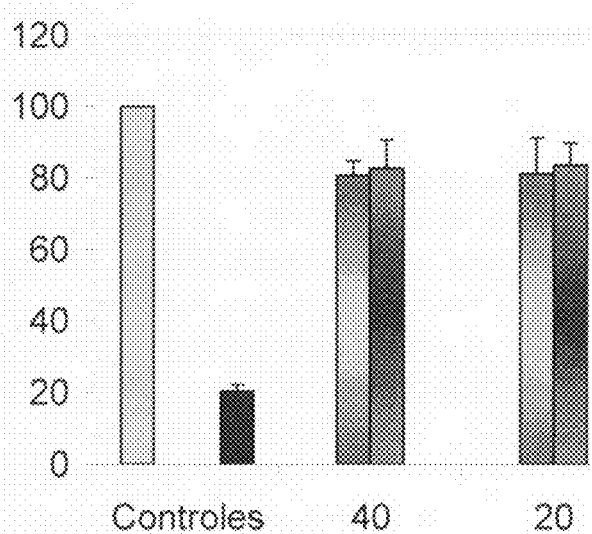

FORMULATION OF LIPOSOMAL VESICLES IN AQUEOUS SOLUTIONS WITH LACHRYMAL FILM CHARACTERISTICS

CROSS-REFERENCE TO RELATED APPLICATION

This application is based on and claims priority from U.S. Provisional Patent Application No. 60/796,118 filed on Apr. 28, 2006 in the United States Patent Office, the disclosure of which is incorporated herein in its entirety by reference.

OBJECTIVE OF THE INVENTION

The present invention refers to a formulation of liposomal vesicles in aqueous solutions which present similar characteristics to the ones of the lachrymal film. The present invention describes a formulation of liposomes in aqueous vehicles. The aqueous vehicles contain mucin or similar substances to mucin or mucomimetic substances or polymers with mucoadhesive properties. The mentioned formulation, at the temperature of the ocular surface, presents similar characteristics to the ones observed in the precorneal tear film in human eye. This mentioned preparation could be used as a substitute of the natural film and it could be used as medicinal preparation in several ocular pathologies such as dry eye syndrome.

This invention is included in the pharmacy and medicine areas.

DESCRIPTION OF THE PRIOR ART

It is known that the ocular surface is formed by the epithelium of the conjuctiva, corneal epithelium, the accessory lachrymal glands and the meibomian glands. The previous mentioned surface is covered by a continuous film with a thickness of 10 μm. This film is known as precorneal film or lachrymal film. Until a few years ago, the theoretical structure of the precorneal film, generally accepted, included three types of components (lipid, aqueous-serous and mucinous) which were distributed in three lipid layers: lipid, aqueous and mucinous. (Ibrahim H, Buri P, Gurny R. Pharm Acta Helv 1988, 63:146-53).

Recently studies consider the precorneal film structure constituted by the aqueous proteinaceous and mucinous components combined to form a hydrated gel. This mentioned gel would be covered by a lipid film which components would be mainly produced by the meibomian glands. This lipid would avoid tear evaporation and improve lachrymal film stability. (Pflugfelder S C, Solomon A, Stern M E. Cornea 2000; 19 (5): 644-649. McCulley J P, Shine W. Tr Am Ophth Soc 1997; 95: 79-93).

According to the proposed model, the precorneal tear film would consist on two phases:

Hydrophilic polar phase that is in contact with the aqueous-mucinous layer which is composed by phospholipids (PL), sphingomieline, ceramides and cerebrosides.

Non polar hydrophobic phase that is in contact with the atmosphere and it is composed by non polar lipids as wax esters, cholesterol esters, triglycerides, free fatty acids and hydrocarbons.

Approximately, the fraction of phospholipids represents between 1 to 5% of the whole lipid secretion being the one of higher concentration phosphatidilcholine (PC) in a percentage near to 40% of the whole amount of phospholipids. Others phospholipids as phosphatidilethanolamine are in a percentage of 18%. The rest of phospholipids (10) are between 3 and 9%. Probably, this fraction produces a surface tension decrease of the aqueous phase making easier the precorneal film extensibility during blinking.

The usual treatment of dry eye consists on the symptomatic relief with the application of artificial tears formulations by topical route. A typical composition of these preparations includes polymeric solutions as described in the U.S. Pat. No. 4,973,580 (Babiole) in which the ophthalmic formulation includes hyaluronic acid employing hydrogen peroxide as preservative. There are several descriptions of formulations in which similar components of the lachrymal film are included. An example of this kind of formulation is the one containing lecithin and viscous agents derived from cellulose as collected in U.S. Pat. No. 4,421,748 (Trager). Several patents include the use of phospholipids for dry eye treatment. Emulsions with positive charged phospholipids are described in U.S. Pat. No. 4,804,539 (Guo) (1989) and U.S. Pat. No. 4,818,537 (Guo). In these patents positive charged liposomes are employed and they are suspended in aqueous solutions with high viscosity polymers as hydroxiethylcellulose, methylcellulose, hydroxipropylmethylcellulose and vinilic derivatives as polyvinilpirrolidone, polyvinilalcohol and their mixtures. Emulsions containing phospholipids, non polar oils and emulsifying agents are cited too U.S. Pat. No. 6,656,460 (Benita).

None of these patents includes the use of neutral liposomes or negative charged liposomes able to be destabilised at the precorneal film surface temperature, associated with mucine or mucoahesive substances or substances similar to mucin or mucomimetics substances as the case of the invention described below.

DESCRIPTION OF THE INVENTION

The method of invention here described involves the preparation of a pharmaceutical formulation which acts as a precorneal film substitute. The formulation includes liposomal vesicles of phospholipids as hydrophilic polar phase and non polar lipids. Both PL are incorporated in aqueous solutions that contain mucin or substances with similar properties to mucin or mucomimetic substances or mucoadhesive polymers. The more relevant advantages of this invention consist on the use of phosphatidilcholine which presents a transition temperature lower than the temperature of the corneal surface. Furthermore this formulation includes polymers or mucoadhesive substances and/or mucomimetics substances (mucine or polymers as hyaluronic acid, cellulose derivatives, chondroitin sulphate, chitosan, colominic acid, thiolic derivatives or other similar component).

The components of the formulation and specifically the phospholipids which compose the liposomes allow the formation of a monomolecular insoluble film on the corneal surface after the liposomal vesicles destabilisation. The insoluble film acts avoiding the evaporation of the aqueous phase and diminishing the surface tension of the aqueous phase improving the fast spreading of the film on the corneal surface. The liposomes are prepared with phosphatidilcholine obtained from soy lecithin as mainly component, cholesterol and α-tocopherol. The phosphatidilcholine contains acyl rests of insaturated fatty acids that lead a transition temperature of the phospholipid lower than the temperature of the corneal surface. This fact allows the formation of the film over the aqueous phase once the formulation is administered on the corneal surface. In its turn, this film is stabilised by cholesterol because this compound reduces the fluidity of the matrix formed by the polyunsaturated rest of the phosphatidilcholine. Finally, the α-tocopherol assures the chemical stability of double bonds avoiding the possibility of peroxidation.

Liposomes are vehiculized in aqueous solution including an isotonic agent (trehalose, sodium chloride, glucose) in order to obtain an adequate osmolarity for their clinical use. Solutions could be isotonics and hypotonics. Once formed, the liposomes are incorporated to aqueous solutions including one or several substances or polymers with mucoadhesive or mucomimetic characteristics to increase the contact time of the formulation and the components of destabilised liposomes on the corneal surface. Once formed the new film is maintained longer avoiding aqueous evaporation from the corneal surface. The concentrations of this last component will depend on the desired final viscosity in the formulation, its interaction with mucin, surface tension and the rheologic behaviour expected after its administration. Proteins are included too in the formulation to increase the stability of the formed film and to improve their lubricant properties. These proteins are found in the natural tears and they can be α-macroglobuline, lysozyme, lipocalin and lactoferrine.

Several components can be added to this formulation. Most of them are components of the natural tear film and they improve the formation characteristics and the time of permanence of the precorneal film and/or act as epithelial forming agents, anti-inflammatory agents and antioxidant agents of the ocular surface, and/or to favour the corneal and conjunctival epithelial differentiation. Among these substances are the following:

Mucoadhesive polymers as hyaluronic acid, cellulose derivatives, chondroitin sulphate, chitosan, colominic acid, thiolic derivatives (or similar components).

Neutral lipids and low polarity lipids as wax, cholesterol esters, triglycerides, free fatty acids and hydrocarbons Vitamin A.

Ions as Sodium, Potassium, Calcium, Chloride and Bicarbonate.

Vitamin C

Albumin or pre-albumine

Immunoglobulin A (IGA).

Epithelial growth factor: EGF).

Beta transforming growth factor (TGF-β).

Acidic fibroblast growth factor (aFGF).

Basic fibroblast growth factor (bFGF).

Antiproteases as macroglobulin.

Neuronal factors as Substance P e insulin like growth factor.

Antibacterial agents as Immunoglobulin G (IgG), lysozime and complement.

Long chain fatty acids as gadoleic, palmitic, palmitoleic, estearic, oleic, linoleic, araquidic, linolenic, eicosenic, lignoceric, lactic and miristic.

Hydrophilic lipids as phospholipids, esphingomieline, ceramides and cerebrosides.

DETAILED DESCRIPTION OF THE INVENTION

The present invention involves the formulation of liposomal vesicles in aqueous solutions which possess lachrymal film properties. The invention is additionally illustrated with the following examples which do not limit the content and the claims included in this patent that are defined for the claims related later.

The liposomal vesicles described in the present invention were prepared according the method described previously by Bangham. To this, phosphatidilcholine, cholesterol and α-tocopherol (in different proportions) were dissolved in chloroform to obtain a final concentration of phosphatidilcholine of 8 mg/ml. The solution, previously satured with nitrogen, was introduced in a rotary evaporator at 30-34° C. with moderate vacuum. After solvent evaporation a thin lipid film was formed on the bottle walls. Once formed the lipid film was hydrated with an aqueous solution containing the isotonic agent, satured with nitrogen, at 37° C. using glass beads that allow the formation of multilamelar vesicles. The final concentration of phosphatidilcholine was adjusted with the isotonic vehicle.

Once prepared, the dispersion was maintained in repose and in dark conditions for two hours. Then, the dispersion was sonicated maintaining the temperature of the product between 5 and 10° C. with ice. The preparation ended with 5 filtrations through a filter of 0.8 µm.

The mucin or mucoadhesive and/or mucomimetic substance was added when the liposomes were diluted to the desired final concentration. Final concentrations of liposomes in the polymeric solutions can be found between 1 mg/ml and 40 mg/ml.

The rest of possible components are added, in function of their physicochemical characteristics, with the isotonic agent or with the mucomimetic substances.

The basic liposomes were prepared with phosphatidilcholine from soybean and cholesterol (8:1) and they were reconstituted with water and hypotonic solutions of sodium chloride. The influence of sonication process on the final size of vesicles was studied by comparing the use of ultrasounds probe for 2.5 minutes and ultrasounds bath for 15 minutes (FIG. 1). The process yield of lipid vesicles preparation, in both cases, resulted higher than 90%.

Dispersion of liposomes in water, at PC concentration of 20 mg/ml, presented pH values between 6.9 and 7.2. The mean diameters for the different batches prepared with ultrasounds bath were between 392 and 478 nm. In all cases, the percentage of particles higher than 1 ?m resulted lower than 2%.

Surface tension measurements were carried out with solutions of different liposomal concentrations, and the data obtained are shown in FIG. 2.

Cellular viability assays were carried out with hypotonic solutions of basic liposomes and basic liposomes with vitamin E in macrophages cell culture. Cytotoxicity studies were performed by the mitocohondrial-dependent reduction of the tetrazolium salt 3(4,5-dimethylthiazol-2yl)-2,5-diphenyltetrazolium bromide) to formazan (MTT method) (Mossman T. J Immune Methods 1983, 65:55-63). Peritoneal macrophages were obtained from Swiss male mice. Culture medium was used as negative control and benzalconium chloride (0.005%) as positive control. Solutions were incubated at 37° C. for 1 and 4 hours. The results showed an optimal tolerance for the basic liposomes with and without vitamin E addition. (FIGS. 3 and 4).

BRIEF DESCRIPTIONS OF THE FIGURES

FIG. 1: Influence of the sonication process on the final size (µm) of vesicles by comparing an ultrasounds probe for 2.5 minutes (-♦-) and ultrasonic bath for 15 minutes (-■-).

FIG. 2: Surface tension measurements (mN/m) of the aqueous dispersions of liposomes at different concentrations. The concentration of liposomes in the solution is expressed as PC concentration (mM).

FIG. 3: Results of cell viability of hypotonic aqueous solutions of basic liposomes with (■) and without (□)

vitamin E addition. Samples were incubated at 37° C. for 4 hour. Solutions containing two concentrations of liposomes (20 and 40 mg/ml) were studied. Culture medium was used as negative control and benzalconium chloride (0.005%) as positive control.

FIG. 4: Results of cell viability of hypotonic aqueous solutions of basic liposomes with (■) and without (■) vitamin E addition. Samples were incubated at 37° C. for 4 hour. Solutions containing two concentrations of liposomes (20 and 40 mg/ml) were studied. Culture medium was used as negative control and benzalconium chloride (0.005%) as positive control.

It is claimed:

1. An ophthalmic composition for use as a precorneal film substitute, comprising phosphatidylcholine liposomal vesicles obtained from soy lecithin containing α-tocopherol and cholesterol, wherein the liposomal vesicles, once formed, are dispersed in aqueous solution with trehalose and hyaluronic acid, and wherein the trehalose is present in the composition in an amount effective to render the ophthalmic composition isotonic or hypotonic in clinical use in a human eye.

2. The composition of claim 1, comprising neutral lipids, low polarity lipids as wax, cholesterol esters, triglycerides, free fatty acids and hydrocarbons.

3. The composition of claim 1, comprising lipocalins.

4. The composition of claim 1, comprising vitamin A.

5. The composition of claim 1, comprising the following ions: Sodium, Potassium, Calcium, Chloride and Bicarbonate.

6. The composition of claim 1, comprising vitamin C.

7. The composition of claim 1, comprising lactoferrine.

8. The composition of claim 1, comprising albumin or prealbumin.

9. The composition of claim 1, comprising immunoglobulin A (IgA).

10. The composition of claim 1, comprising an antibacterial agent selected from the group consisting of Immunoglobulin G (IgG), lysozyme and a complement thereof.

11. The composition of claim 1, comprising a long chain fatty acid selected from the group consisting of gadoleic, palmitic, palmitoleic, estearic, oleic, linoleic, araquidic, linolenic, eicosenic, lignoceric, lactic and miristic.

12. The composition of claim 1, comprising a hydrophilic lipid selected from the group consisting of phospholipids, sphingomyelin, ceramides and cerebrosides.

13. The composition of claim 1, comprising a growth factor.

14. The composition of claim 13, wherein the growth factor comprises epithelial growth factor: EGF.

15. The composition of claim 13, wherein the growth factor comprises beta transforming growth factor (TGF-β), acidic fibroblast growth factor (aFGF), basic fibroblast growth factor (bFGF), or Substance P insulin-like growth factor.

16. The composition of claim 13, which comprises an antiprotease.

17. The ophthalmic composition according to claim 1, wherein the trehalose is present in the composition in an amount effective to render the ophthalmic composition isotonic in clinical use in a human eye.

18. The ophthalmic composition according to claim 1, wherein the trehalose is present in the composition in an amount effective to render the ophthalmic composition hypotonic in clinical use in a human eye.

19. A method for treating dry eye syndrome in a patient in need of such treatment comprising providing the composition of claim 1, and applying the composition to an eye of the patient.

* * * * *